(12) United States Patent
Soeda et al.

(10) Patent No.: US 9,572,594 B2
(45) Date of Patent: Feb. 21, 2017

(54) ATHERECTOMY CATHETER

(71) Applicant: NIPRO CORPORATION, Osaka (JP)

(72) Inventors: Nobuyuki Soeda, Fukushima (JP); Katsuya Miyagawa, Osaka (JP); Yuuki Nishimura, Osaka (JP); Misa Kakinoki, Osaka (JP)

(73) Assignee: NIPRO CORPORATION, Osaka (JP)

( * ) Notice: Subject to any disclaimer, the term of this patent is extended or adjusted under 35 U.S.C. 154(b) by 338 days.

(21) Appl. No.: 14/360,715

(22) PCT Filed: Oct. 30, 2012

(86) PCT No.: PCT/JP2012/078051
§ 371 (c)(1),
(2) Date: May 27, 2014

(87) PCT Pub. No.: WO2013/080729
PCT Pub. Date: Jun. 6, 2013

(65) Prior Publication Data
US 2014/0343584 A1 Nov. 20, 2014

(30) Foreign Application Priority Data
Nov. 28, 2011 (JP) ................................. 2011-258406

(51) Int. Cl.
*A61B 17/3207* (2006.01)
*A61M 25/00* (2006.01)
(Continued)

(52) U.S. Cl.
CPC .................. *A61B 17/320783* (2013.01); *A61B 17/320758* (2013.01); *A61M 25/0023* (2013.01);
(Continued)

(58) Field of Classification Search
CPC ............... A61B 17/320783; A61B 17/320758; A61B 17/3207; A61B 17/32075; A61B 2017/22071; A61B 2017/320064; A61B 2017/320791; A61B 2017/320766; A61B 2017/320775; A61B 2017/320741; A61B 17/32002; A61M 25/007; A61M 25/0026; A61M 25/0023
(Continued)

(56) References Cited

U.S. PATENT DOCUMENTS 4,696,667 A 9/1987 Masch
5,470,415 A 11/1995 Perkins et al.
(Continued)

FOREIGN PATENT DOCUMENTS

JP 62-270140 11/1987
JP 2-121648 5/1990
(Continued)

*Primary Examiner* — Katrina Stransky
(74) *Attorney, Agent, or Firm* — Jordan and Koda, PLLC (57) ABSTRACT

An atherectomy catheter has a shaft having an opening in the side wall, a cutter which is positioned near the opening in the internal space of the shaft and which can move in the axial direction of the shaft, and a distal end portion connected to the distal end of the shaft. The distal end portion has a blade tube connected to the distal end of the shaft by continuing the internal space, a reduced diameter portion connected to the distal end of the blade tube by continuing the internal space, and a distal end tip whose outer diameter is smaller than the outer diameter of the distal end of the blade tube, whose distal end side is projected outward from the distal end of the reduced diameter portion, and whose proximal end side is extended into the internal space of the blade tube through the internal space of the reduced diameter portion.

17 Claims, 5 Drawing Sheets

(51) Int. Cl.
*A61B 17/22* (2006.01)
*A61B 17/32* (2006.01)

(52) U.S. Cl.
CPC ............... *A61B 2017/22071* (2013.01); *A61B 2017/320064* (2013.01)

(58) Field of Classification Search
USPC ........................................................ 606/159
See application file for complete search history.

(56) References Cited

U.S. PATENT DOCUMENTS

| | | |
|---|---|---|
| 5,507,795 A | 4/1996 | Chiang et al. |
| 2002/0077642 A1 | 6/2002 | Patel et al. |
| 2006/0064123 A1 | 3/2006 | Bonnette et al. |
| 2009/0054875 A1* | 2/2009 | Strauss .......... A61B 17/320708 604/528 |

FOREIGN PATENT DOCUMENTS

| | | |
|---|---|---|
| JP | 5-56984 | 3/1993 |
| JP | 6-30943 | 2/1994 |
| JP | 2007-089724 | 4/2007 |
| JP | 2011-522591 | 8/2011 |

\* cited by examiner

FIG. 5

ATHERECTOMY CATHETER

TECHNICAL FIELD

The present invention relates to a catheter which is inserted into a blood vessel in order to excise an atheroma adhering to the inner wall of the blood vessel.

BACKGROUND OF THE INVENTION

Heretofore, medical treatment of excising an atheroma arising in a blood vessel by inserting a catheter into the blood vessel has been performed. The catheter for use in the medical treatment has an opening in the side wall. The catheter is inserted into the blood vessel to a position where the opening faces the atheroma. Then, when a balloon provided near the opening is expanded, the opening comes close to the atheroma, and then the atheroma enters a lumen of the catheter through the opening. In the lumen of the catheter, a cutter is provided movably in the axial direction. The cutter is driven by a motor to be rotated in the lumen. Due to the fact that the cutter is made to move in the lumen while being rotated, the atheroma entering the lumen is excised. The excised atheroma is stored in the lumen of the catheter (Citation List 1 and 2).

The catheter described above is inserted into the blood vessel while being guided by a guide wire. For example, in the coronary artery, the blood vessel itself curves in many cases, and therefore when the catheter is inserted into the blood vessel, the distal end of the catheter contacts the inner wall of the blood vessel in many cases. Therefore, it is desired that the distal end of the catheter has such flexibility that the distal end of the catheter follows the shape of the blood vessel and does not damage the inner wall of the blood vessel. For example, a so-called nose cone is known as the structure of the distal end of the catheter (Patent Literature 3). The nose cone is a structure in which a spiral wire is provided as the core in a resin tube. Moreover, a marker detectable by X-rays is provided on the distal end of the nose cone.

CITATION LIST

PTL 1: Japanese Unexamined Patent Application Publication No. 6-30943
PTL 2: Japanese Unexamined Patent Application Publication No. 5-56984
PTL 3: Japanese Unexamined Patent Application Publication (Translation of PCT Application) No. 2011-522591

There has been a problem in that the distal end portion of the former catheter described above is likely to bend when the catheter is inserted into the blood vessel. Moreover, it has been desired to increase the amount of the atheroma excised by the cutter which can be stored in the lumen in such a manner as to be able to excise a large atheroma.

The present invention has been made in view of the above-described circumstances. It is an object of the present invention to provide a measure capable of flexibly changing the posture when inserted into a blood vessel and increasing the storable amount of an excised atheroma.

SUMMARY OF THE INVENTION (1) An atherectomy catheter according to the present invention has a first tubular body which has an opening in the side wall and whose distal end is opened, a cutter which is positioned near the opening in the internal space of the first tubular body and which can move in the axial direction of the first tubular body, and a distal end portion connected to the distal end of the first tubular body. The distal end portion has a resin second tubular body which is connected to the distal end of the first tubular body by continuing the internal space and whose rigidity is higher than that of the first tubular body, a resin third tubular body which is connected to the distal end of the second tubular body by continuing the internal space and whose diameter is reduced in a tapered shape from the distal end of the second tubular body, and a resin fourth tubular body whose outer diameter is smaller than the outer diameter of the distal end of the second tubular body, whose first end side is projected outward from the distal end of the third tubular body, and whose second end side is extended into the internal space of the second tubular body through the internal space of the third tubular body.

Since the diameter of the third tubular body decreases in a tapered shape at the distal end of the second tubular body and is connected to the fourth tubular body whose diameter is smaller than that of the second tubular body, the distal end portion of the atherectomy catheter is easily inserted into a blood vessel even when the diameter of the second tubular body is increased to increase the capacity of the internal space. Moreover, since the second end side of the fourth tubular body is extended into the internal space of the second tubular body through the internal space of the third tubular body, the third tubular body and the fourth tubular body form a double tube structure, so that the strength of a portion corresponding to the third tubular body is increased.

(2) An atherectomy catheter according to the present invention has a first tubular body which has an opening in the side wall and whose distal end is opened, a cutter which is positioned near the opening in the internal space of the first tubular body and which can move in the axial direction of the first tubular body, and a distal end portion connected to the distal end of the first tubular body. The distal end portion has a resin second tubular body which is connected to the distal end of the first tubular body by continuing the internal space and is reinforced by a core material, a resin third tubular body which is connected to the distal end of the second tubular body by continuing the internal space and whose diameter is reduced in a tapered shape from the distal end of the second tubular body, and a resin fourth tubular body whose outer diameter is smaller than the outer diameter of the distal end of the second tubular body, whose first end side is projected outward from the distal end of the third tubular body, and whose second end side is extended into the internal space of the second tubular body through the internal space of the third tubular body.

(3) The core material may be formed into a tubular shape by netting a wire.

(4) On the inner surface side of the second tubular body, a cylindrical member to be connected to the first tubular body and a wire extended from the cylinder member to the third tubular body side may be provided.

(5) The wire may form a spiral shape.

(6) The second end side of the fourth tubular body may have a diameter increased in a tapered shape. This facilitates the insertion of a guide wire from the second end side of the fourth tubular body.

(7) The fourth tubular body may have a through-hole in the side wall on the second end side.

(8) The first tubular body may have a balloon which expands outward from the side wall.

Advantageous Effects of Invention

According to the atherectomy catheter according to the present invention, the diameter is reduced in a tapered shape from the second tubular body by the third tubular body, and the third tubular body is connected to the fourth tubular body, and therefore the distal end portion flexibly changes the posture when inserted into a blood vessel. Moreover, since the diameter of the second tubular body can be increased, the storable amount of an excised atheroma can be increased.

DESCRIPTION OF THE PREFERRED EMBODIMENTS

Hereinafter, a preferable embodiment of the present invention is described. This embodiment is merely one embodiment of the present invention and it is a matter of course that the embodiment can be altered in a range where the gist of the present invention is not altered.

Figure 1:
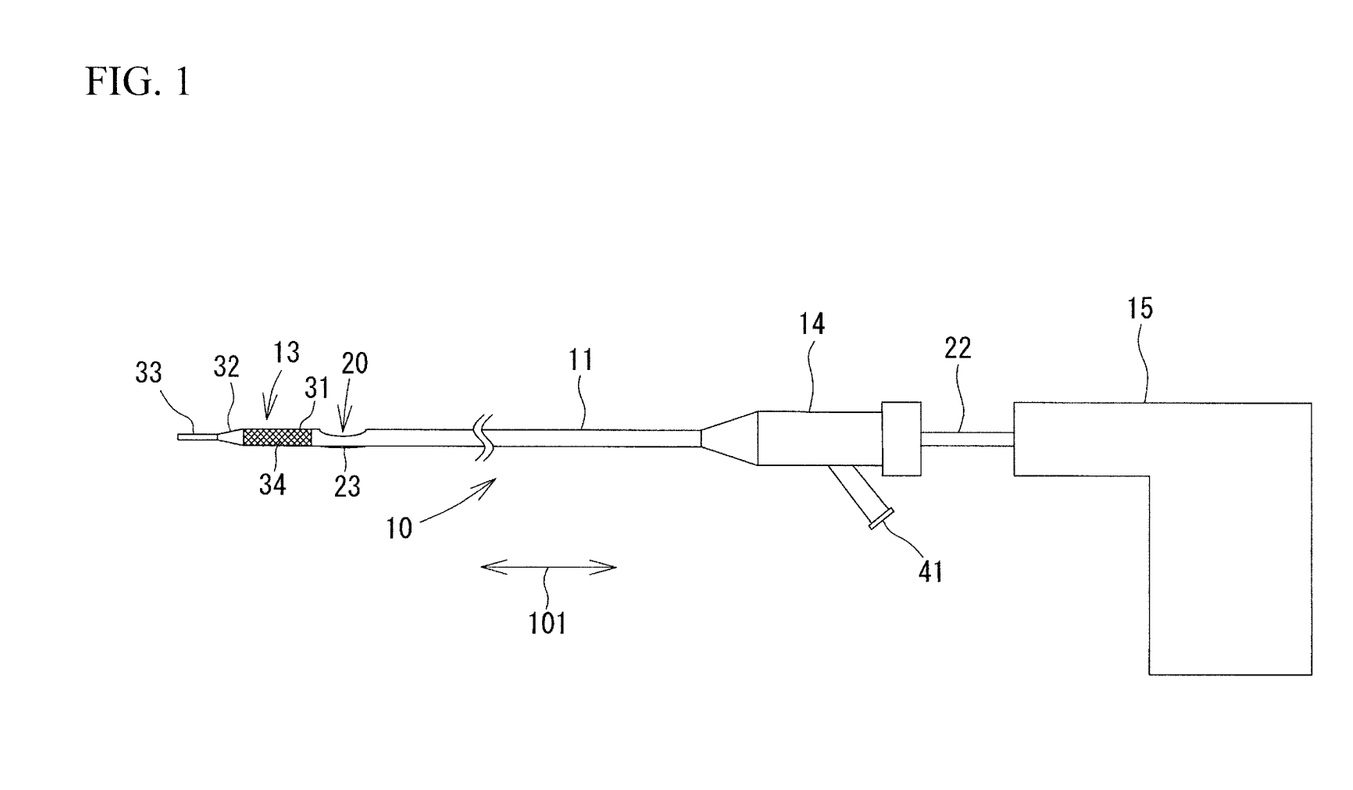
FIG. 1 is a view illustrating the configuration of the appearance of an atherectomy catheter in a state where a balloon is contracted.
Figure 2:
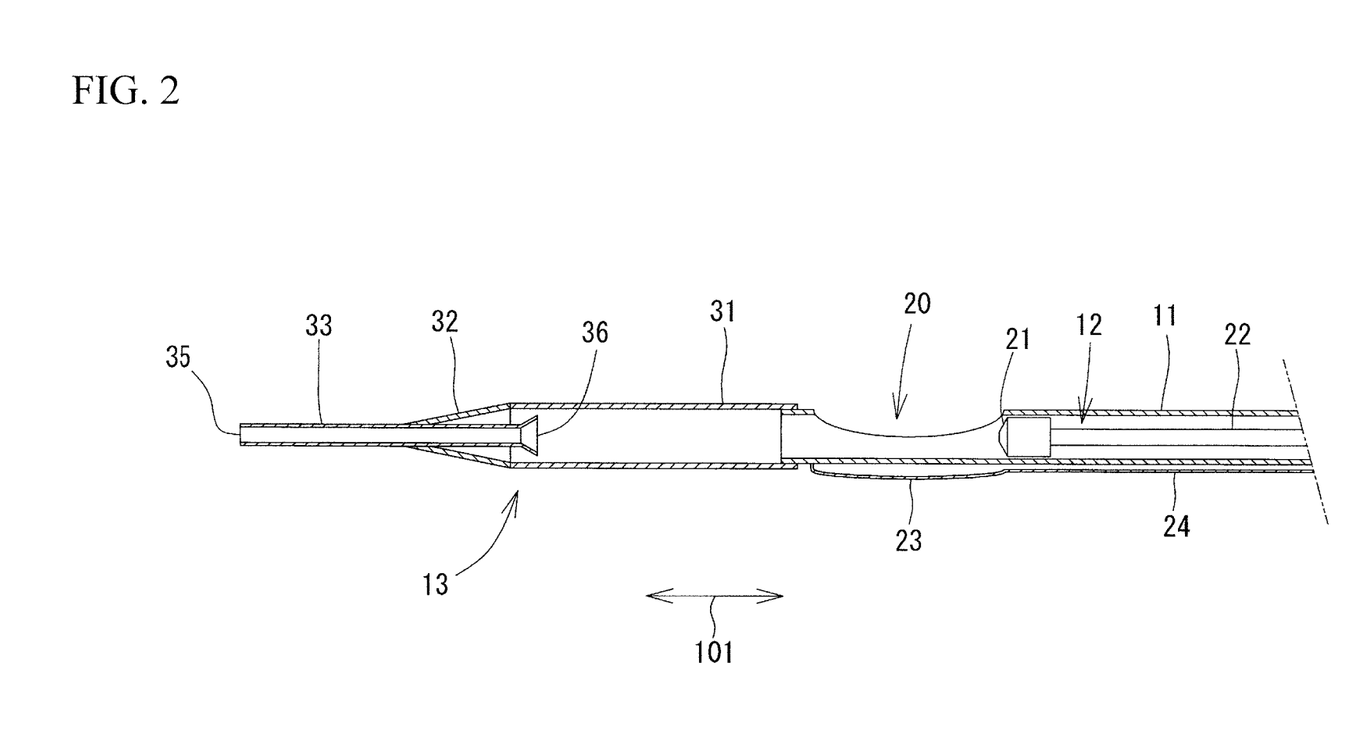
FIG. 2 is an enlarged cross sectional view illustrating the internal configuration near a distal end portion of the atherectomy catheter.

As illustrated in FIGS. 1 and 2, the atherectomy catheter 10 has a shaft 11, a cutter 12 provided in the shaft 11, a distal end portion 13 constituting the distal end of the shaft 11, a proximal end portion 14 connected to the proximal end of the shaft 11, and an actuator 15 which gives drive-for-rotation to the cutter 12. The atherectomy catheter 10 is used as a medical implement which is inserted into a blood vessel to excise an atheroma.

The shaft 11 is a tube capable of containing the cutter 12 inside. The shaft 11 is constituted by a cylindrical tube containing a stainless steel for medical treatment or a cylindrical tube containing a synthetic resin, for example, and has flexibility which allows the shaft 11 to elastically curve according to the curved shape of a blood vessel. The distal end and the proximal end of the shaft 11 each open. The outer diameter of the shaft 11 is set according to the inner diameter of a blood vessel into which the shaft 11 is to be inserted, for example, the coronary artery. The inner diameter of the shaft 11 is set according to the outer diameter of the cutter 12. The outer diameter and the inner diameter of the shaft 11 are almost equal over the axial direction 101 of the shaft 11. The length in the axial direction 101 of the shaft 11 is set considering the length from the catheter insertion portion to the affected portion, such as the human limbs.

As illustrated in FIG. 2, in the shaft 11, an opening 20 is formed near the distal end portion 13. The opening 20 is formed by partially cutting the side wall of the shaft 11. The shape and the size of the opening 20 are set considering the shape and the size of an atheroma which may be formed in the affected portion. The shaft 11 is equivalent to the first tubular body.

As illustrated in FIG. 2, in the internal space of the shaft 11, the cutter 12 is provided near the opening 20. The cutter 12 has a cutting portion 21 and a shaft 22. The cutting portion 21 has almost a cylindrical shape and the outer diameter is a little smaller than the inner diameter of the shaft 11. On the distal end side of the cutting portion 21, a plurality of edges are formed in such a manner as to radially extend from the center. Although not illustrated in FIG. 2, a through-hole is formed in the center of the cutting portion 21 along an axial direction 101. The shaft 22 is extended from the proximal end of the cutting portion 21 to the outside of the proximal end portion 14. The shaft 22 is a narrow and long tube and the internal space communicates with the through-hole of the cutting portion 21. The internal space of the shaft 22 and the through-hole of the cutting portion 21 are those for passing a guide wire.

As illustrated in FIG. 1, the shaft 22 is connected to the actuator 15. When the shaft 22 is driven by the actuator 15 to rotate, the cutting portion 21 rotates. Moreover, when the shaft 22 is moved in the axial direction 101, the cutting portion 21 moves in the axial direction 101 in the internal space of the shaft 11.

As illustrated in FIGS. 1 and 2, a balloon 23 is provided at a position opposite to the opening 20 in the shaft 11. The balloon 23 can expand outward from the side wall of the shaft 11 and is folded and adheres to the side wall of the shaft 11 until the atherectomy catheter 10 is inserted into a blood vessel. The material of the balloon 23 is preferably a material having biocompatibility and specifically includes polyurethane, polyethylene, polyester, polypropylene, polyamide, a polyamide elastomer, polytetrafluoroethylene, polyvinylidene fluoride, and the like.

As illustrated in FIG. 2, the proximal end side of the balloon 11 is connected to an outer tube 24 provided along the side wall of the shaft 11. The internal space of the outer tube 24 is made to communicate with the internal space of the balloon 11. The outer tube 24 is extended to the proximal end portion 14 and the internal space of the outer tube 24 is continuous to a port 41 of the proximal end portion 14. When liquid, such as physiological saline, injected from the port 41 of the proximal end portion 14 flows into the balloon 11, the balloon 23 expands in a blood vessel. The outer tube 24 is a molded body of a soft plastic which can elastically deform, such as polyamide, a polyamide elastomer, and polyetheramide.

As illustrated in FIGS. 1 and 2, the distal end portion 13 is connected to the distal end of the shaft 11. As illustrated in FIG. 2, the distal end portion 13 has a blade tube 31, a reduced diameter portion 32, and a distal end tip 33.

As illustrated in FIGS. 1 and 2, the blade tube 31 is a cylindrical tube whose both sides open. The blade tube 31 is connected to the distal end of the shaft 11 and the internal space is made to communicate with the internal space of the shaft 11. The blade tube 31 is one in which a soft plastic which can elastically deform, such as polyamide, a polyamide elastomer, and polyetheramide, is reinforced by a core material 34. The core material 34 is embedded in the side wall of the blade tube 31. More specifically, the blade tube 31 forms a two-layer structure of an inner layer and an outer layer which contain the soft plastic described above and the core material 34 is sandwiched between the layers to be embedded in the blade tube 31. The core material 34 is formed into a tubular shape by netting a wire, such as stainless steel for medical treatment. The rigidity of the side wall of the blade tube 31 is increased by the core material 34. The inner diameter of the blade tube 31 is almost equal to the outer diameter of the shaft 11 and the blade tube 11 is fitted into the distal end of the shaft 11 from the outside. The outer diameter and inner diameter of the blade tube 31 are almost equal over the axial direction 101. The blade tube 31 is equivalent to the second tubular body. In FIG. 2, the illustration of the core material 34 is omitted.

As illustrated in FIGS. 1 and 2, the reduced diameter portion 32 is a cylindrical tube whose both sides open and whose outer diameter decreases in a tapered shape. The reduced diameter portion 32 is connected to the distal end of the blade tube 31 and the internal space is continuous to the internal space of the blade tube 31. The reduced diameter portion 32 contains a soft plastic which can elastically deform, such as polyamide and polyetheramide. The inner diameter on the proximal end side of the reduced diameter portion 32 is almost equal to the outer diameter of the distal end of the blade tube 31. The reduced diameter portion 32 is fitted into the distal end of the blade tube 31 from the outside and thermally fused. The inner diameter on the distal end side of the reduced diameter portion 32 is almost equal to the outer diameter of the central portion of the distal end tip 33. On the distal end side of the reduced diameter portion 32, the thickness decreases toward the distal end side. The reduced diameter portion 32 is equivalent to the third tubular body.

As illustrated in FIGS. 1 and 2, the distal end tip 33 is a cylindrical tube whose both sides open and whose outer diameter on the proximal end 36 side increases in a tapered shape. The distal end tip 33 is connected to the distal end of the reduced diameter portion 32 and the internal space is continuous to the internal space of the reduced diameter portion 32. A distal end 35 of the distal end tip 33 is projected outward in the axial direction 101 from the distal end of the reduced diameter portion 32. The proximal end 36 side of the distal end tip 33 extends the internal space of the reduced diameter portion 32 in the axial direction 101 and the proximal end 36 reaches the internal space of a blade tube 31. More specifically, in a region from the distal end side portion of the blade tube 31 to the reduced diameter portion 32, a double tube structure is formed in which the blade tube 31 and the reduced diameter portion 32 serve as the outer side and the distal end tip 33 serves as the inner side.

The distal end tip 33 has a diameter increased on the proximal end 36 side but the outer diameter and the inner diameter of the other portion are almost equal. The outer diameter of the diameter equal portion is smaller than the inner diameter of the blade tube 31 and is almost equal to the inner diameter of the distal end of the reduced diameter portion 32. The diameter of the proximal end 36 side of the distal end tip 33 is increased but the maximum diameter is smaller than the inner diameter of the blade tube 31. Therefore, in the internal space of the blade tube 31 and the reduced diameter portion 32, a space is present between the outer surface of the distal end tip 33 and the inner surface of the blade tube 31 and the inner surface of the reduced diameter portion 32.

The distal end tip 33 contains a soft plastic which can elastically deform, such as polyamide and polyetheramide. The distal end tip 33 is inserted into the distal end of the reduced diameter portion 32 and is thermally fused. The distal end tip 33 is equivalent to the fourth tubular body. A marker which can be confirmed by X-rays and the like may be provided on the distal end of the distal end tip 33.

On the proximal end of the shaft 11, a proximal end portion 14 is provided. The proximal end portion 14 is a cylindrical member having an internal space continuous to the internal space of the shaft 11. The proximal end portion 14 is a molded body of resin, such as polypropylene and ABS. The proximal end portion 14 may serve as a handle in an operation of inserting or removing the shaft 11 into/from a blood vessel.

The proximal end portion 14 is provided with a port 41 extended in a direction crossing to the axial direction 101. When another device, such as a syringe, is connected to the port 41, fluid, such as physiological saline, which is made to flow into/out of another device flows into/out of the outer tube 24 from the proximal end portion 14. The proximal end portion 14 may be provided with another port continuous to the internal space of the shaft 11. Such a port is used for the purpose of, for example, collecting an excised acheroma and the like entering the inside of the shaft 11.

From the opening on the proximal end side of the proximal end portion 14, a shaft 22 of the cutter 12 is extended and the actuator 15 is connected to the shaft 22. The actuator 15 contains a motor, a battery, and the like. The rotation of the motor of the actuator 15 is transmitted to the shaft 22.

Hereinafter, the directions for use of the atherectomy catheter 10 are described with reference to FIGS. 3 and 4.

The atherectomy catheter 10 is used when excising the atheroma 51 formed in the inner wall of the blood vessel 50. The atherectomy catheter 10 is inserted into the blood vessel 50 from the distal end portion 13 in the state where the balloon 23 is contracted (refer to FIG. 1). Although not illustrated in each figure, when the atherectomy catheter 10 is inserted into the blood vessel 50, a guide wire is inserted into the blood vessel 50 beforehand. The insertion of the guide wire into the blood vessel 50 is performed by a known technique. While the guide wire inserted into the blood vessel 50 being inserted into the internal space of the distal end tip 33 of the distal end portion 13, the internal space of the shaft 11, the through-hole of the cutting portion 21 of the cutter 12, and the internal space of the shaft 22 in the stated order, the atherectomy catheter 10 is inserted into the blood vessel 50 from the distal end portion 13.

In a portion where the blood vessel 50 curves as in the coronary artery, the distal end portion 13 is advanced to the atheroma 51 of the blood vessel 50 while elastically curving along the guide wire. The diameter of the distal end portion 13 is reduced in a tapered shape by the reduced diameter portion 32 and the distal end portion 13 is connected to the distal end tip 33 whose diameter is smaller than that of the blade tube 31. Therefore, even when the inner diameter of the blade tube 31 is increased to increase the capacity of the internal space, the distal end portion 13 is easily inserted into the blood vessel 50 due to the fact that the pro distal end tip 33 which is soft and has a small diameter is present on the distal end side. The blade tube 31 contains the core material 34, so that the rigidity is made higher than that of a soft plastic. In the distal end side of the blade tube 31 and the reduced diameter portion 32, the rigidity is increased by the double tube structure with the distal end tip 33. Therefore, when the distal end portion 13 is inserted into the blood vessel 50, bending in the distal end portion 13 is suppressed.

Figure 3:
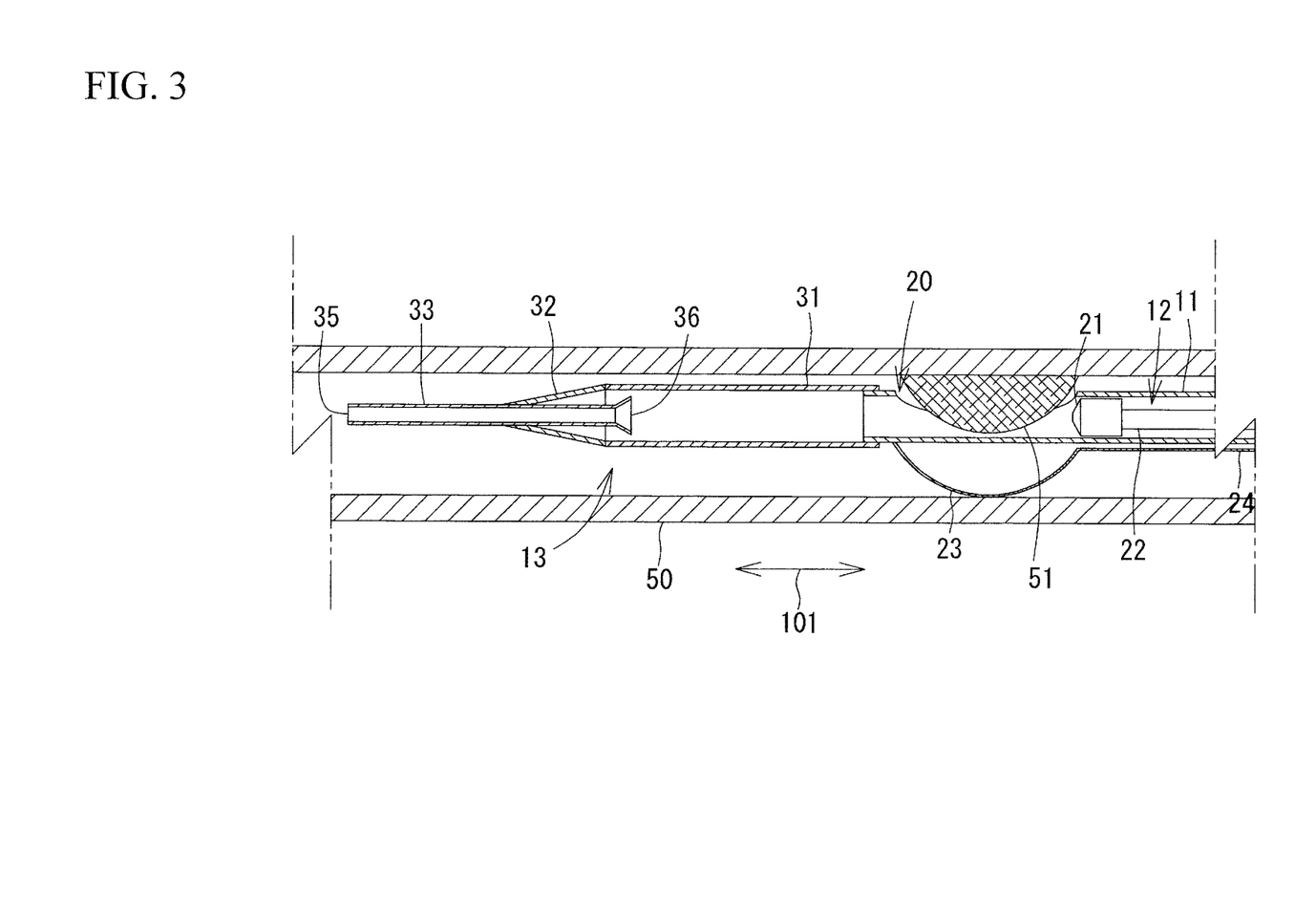
FIG. 3 is a schematic view illustrating a state where the balloon is expanded in a blood vessel.
Figure 4:
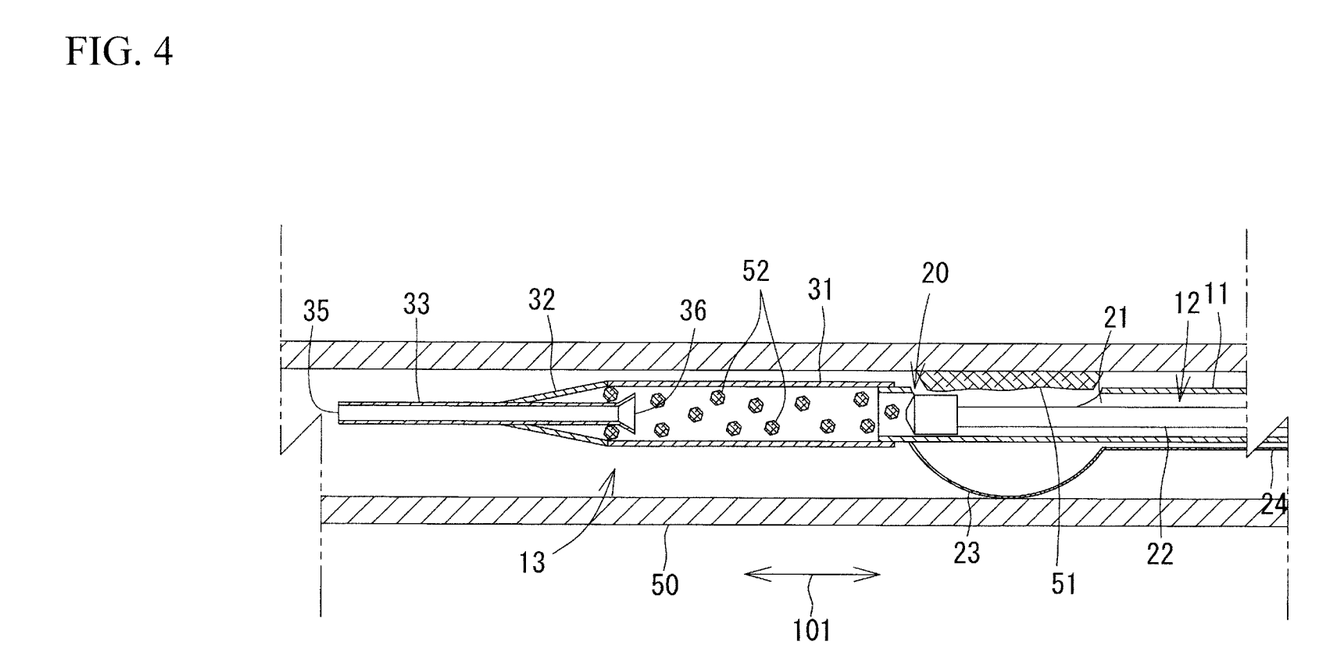
FIG. 4 is a schematic view illustrating a state where an atheroma is excised in the blood vessel.

As illustrated in FIG. 3, when the distal end portion 13 reaches the atheroma 51, and then the opening 20 of the shaft 11 faces the atheroma 51, the insertion of the shaft 11 into the blood vessel 50 is ended. Thereafter, the guide wire is drawn out from the proximal end side of the atherectomy catheter 10. The actuator 15 is connected to the shaft 22 of the cutter 12.

As illustrated in FIG. 3, the balloon 23 in a contracted state is expanded by the fluid which is made to flow into the outer tube 24 from the port 41 in the state where the opening 20 of the shaft 11 faces the atheroma 51. When the expanded balloon 23 abuts to the inner wall of the blood vessel 50 opposite to the atheroma 51, the opening 20 is made to adhere to the atheroma 51, and a part of the atheroma 51 enters the internal space of the shaft 11 from the opening 20.

Subsequently, the motor of the actuator 15 is driven to rotate the cutting portion 21 through the shaft 22 of the cutter 12. When the shaft 22 is made to advance to the distal end side in the axial direction 101 to the shaft 11 on the proximal end portion 14 side, the rotating cutting portion 21 abuts to the atheroma 51, and then the atheroma 51 is excised by the cutting portion 21.

Pieces 52 of the excised atheroma 51 enter the internal space of the blade tube 31 through the internal space of the shaft 11. Since the soft plastic is reinforced by the core material 34 in the blade tube 31, the thickness is not required to increase in order to increase the rigidity even when the inner diameter of the blade tube 31 is increased to increase the capacity of the internal space capable of storing the pieces 52. This suppresses an increase in the outer diameter of the distal end portion 13. Moreover, since the distal end side of the blade tube 31 and the reduced diameter portion 32 form a double tube structure with the distal end tip 33, the pieces 52 can also be stored in the space between the inner surface of the blade tube 31 and the reduced diameter portion 32 and the outer surface of the distal end tip 33.

As described above, when the excision of the atheroma 51 is completed, the balloon 23 is contracted, and then the atherectomy catheters 10 are drawn out to be removed from the blood vessel 50.

As described above, according to the atherectomy catheter 10, the outer diameter is reduced in a tapered shape from the blade tube 31 by the reduced diameter portion 32 and the distal end portion 13 is connected to the distal end tip 33, and therefore the distal end portion 13 flexibly changes the posture when inserted into the blood vessel 50. Moreover, since the diameter of the blade tube 31 can be increased, the storable amount of the pieces 52 of the excised atheroma 50 can be increased.

In this embodiment, the rigidity of the blade tube 31 is higher than that of the shaft 11 by the use of the blade tube 31 reinforced by the core material 34 but the reinforcement by the core material 34 is not indispensable and a tube whose rigidity is higher than that of the shaft 11 may be used in place of the blade tube 31, for example depending on the type, composition, and the like of the synthetic resin.

Figure 5:
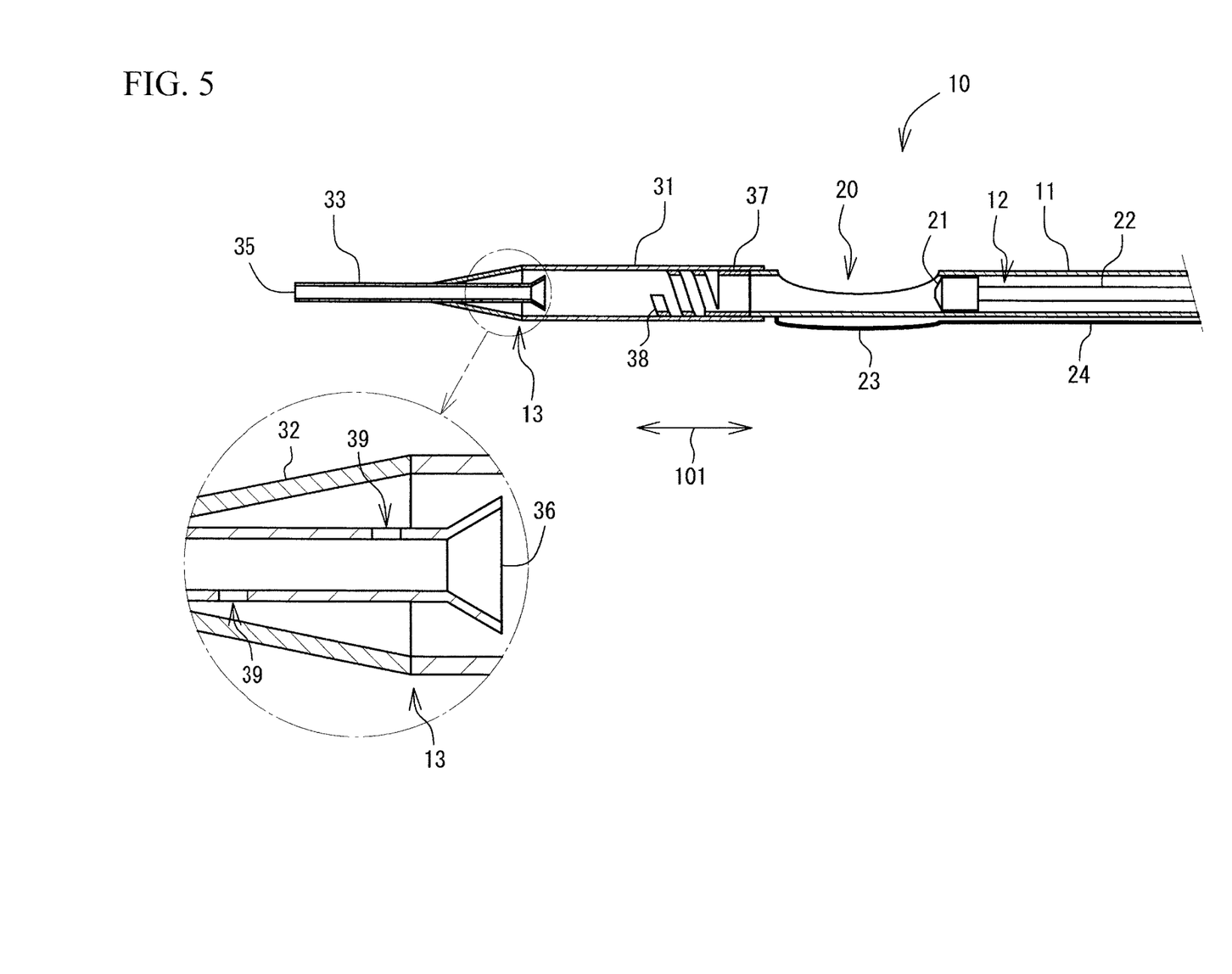
FIG. 5 is an enlarged cross sectional view illustrating a modification of the atherectomy catheter.

Moreover, as illustrated in FIG. 5, a cylindrical member 37 to be connected to the shaft 11 and a wire 38 extended from the cylindrical member 37 to the reduced diameter portion 32 side may be provided on the inner surface side of the blade tube 31. The wire 38 forms a spiral shape along the inner surface side of the blade tube 31. The cylindrical member 37 and the wire 38 are formed, for example, with stainless steel for medical treatment and the like. The wire 38 may be integrally formed with the cylindrical member 37 or one which is formed as another member separately from the cylindrical member 37 may be connected to the cylindrical member 37. Moreover, although not illustrated in FIG. 5, a plurality of linear wires may be disposed with intervals in the diameter direction of the blade tube 31 in place of the spiral wire 38, and extended toward the reduced diameter portion 32 from the cylindrical member 37. Due to the fact that the wire 38 is disposed on the inner surface side of the blade tube 31, the rigidity does not sharply change in the connection portion of the shaft 11 and the blade tube 31, bending does not occur in the connection section, and smooth deformation of the shaft 11 and the blade tube 31 is realized.

Moreover, as illustrated in FIG. 5, a through-hole 39 may be formed in the side wall in a portion which is located on the proximal end 36 side of the distal end tip 33 and is covered with the reduced diameter portion 32. Two through-holes 39 are formed at different positions in the axial direction 101 of the distal end tip 33 and positions where the through-holes 39 face each other with respect to the axis line of the distal end tip 33.

As described above, the pieces 52 of the excised atheroma 51 enters the internal space of the blade tube 31 through the internal space of the shaft 11. The pieces 51 are taken out from the inside of the blade tube 31 in order to analyze the composition after an operation. The pieces 52 are taken out by, for example, a method of making the pieces 52 flow out of the opening 20 by injecting physiological saline from the distal end 35 side of the distal end tip 33. Due to the fact that the physiological saline is made to flow out of not only the proximal end 36 of the distal end tip 33 but the through-hole 39, the pieces 51 stored in the space between the distal end tip 33 and the reduced diameter portion 32 are also made to flow out toward the opening 20.

The number of the through-holes 39 may be one or may be three or more. Moreover, the through-holes 39 may be disposed on the same side with respect to the axis line of the distal end tip 33.

REFERENCE SIGNS LIST

10 . . . Atherectomy catheter
11 . . . Shaft (First tubular body)
12 . . . Cutter
13 . . . Distal end portion
20 . . . Opening
23 . . . Balloon
31 . . . Blade tube (Second tubular body)
32 . . . Reduced diameter portion (Third tubular body)
33 . . . Distal end tip (Fourth tubular body)
35 . . . Distal end (First end)
36 . . . Proximal end (Second end)
37 . . . Cylinder member
38 . . . Wire
39 . . . Through-hole

The invention claimed is:

1. An atherectomy catheter, comprising:
a first tubular body which has an opening in a side wall and whose distal end is opened;
a cutter which is positioned near the opening in an internal space of the first tubular body and which can move in an axial direction of the first tubular body; and
a distal end portion connected to the distal end of the first tubular body, wherein
the distal end portion has:
a resin made second tubular body which is connected to the distal end of the first tubular body by continuing an internal space and whose rigidity is higher than that of the first tubular body;
a resin made third tubular body which is connected to a distal end of the second tubular body by continuing an internal space and whose diameter is reduced in a tapered shape from the distal end of the second tubular body wherein the rigidity of the second tubular body is higher than that of the third tubular body; and a resin made fourth tubular body whose outer diameter is smaller than an outer diameter of the distal end of the second tubular body, whose first end side is projected outward from a distal end of the third tubular body, and whose second end side is extended into the internal space of the third tubular body, and wherein the rigidity of the second tubular body is higher than that of the fourth tubular body.

2. The atherectomy catheter according to claim 1, wherein, on an inner surface side of the second tubular body, a cylindrical member to be connected to the first tubular body and a wire extended from the cylinder member to the third tubular body side are provided.

3. The atherectomy catheter according to claim 2, wherein the wire forms a spiral shape.

4. The atherectomy catheter according to claim 1, wherein a second end side of the fourth tubular body has a diameter increased in a tapered shape.

5. The atherectomy catheter according to claim 1, wherein the fourth tubular body has a through-hole in a side wall on the second end side.

6. The atherectomy catheter according to claim 1, wherein the first tubular body has a balloon which expands outward from the side wall.

7. The atherectomy catheter according to claim 1, wherein the third tubular body and the fourth tubular body form a double tube structure.

8. The atherectomy catheter according to claim 7, wherein there is a gap between the third tubular body and fourth tubular body along at least a partial length of the double tube structure.

9. An atherectomy catheter, comprising:
a first tubular body which has an opening in a side wall and whose distal end is opened;
a cutter which is positioned near the opening in an internal space of the first tubular body and which can move in an axial direction of the first tubular body; and
a distal end portion connected to the distal end of the first tubular body, wherein
the distal end portion has:
a resin made second tubular body which is connected to the distal end of the first tubular body by continuing an internal space and which is reinforced by a core material;
a resin made third tubular body which is connected to a distal end of the second tubular body by continuing an internal space and whose diameter is reduced in a tapered shape from the distal end of the second tubular body and which is not reinforced by a core material; and
a resin made fourth tubular body whose outer diameter is smaller than an outer diameter of the distal end of the second tubular body, whose first end side is projected outward from a distal end of the third tubular body, and whose second end side is extended into the internal space of the third tubular body, and which is not reinforced by a core material.

10. The atherectomy catheter according to claim 9, wherein the core material of the second tubular body is formed into a tubular shape by netting a wire.

11. The atherectomy catheter according to claim 10, wherein the third tubular body and the fourth tubular body form a double tube structure.

12. The atherectomy catheter according to claim 11, wherein there is a gap between the third tubular body and fourth tubular body along at least a partial length of the double tube structure.

13. The atherectomy catheter according to claim 9, wherein, on an inner surface side of the second tubular body, a cylindrical member to be connected to the first tubular body and a wire extended from the cylinder member to the third tubular body side are provided.

14. The atherectomy catheter according to claim 13, wherein the wire forms a spiral shape.

15. The atherectomy catheter according to claim 9, wherein a second end side of the fourth tubular body has a diameter increased in a tapered shape.

16. The atherectomy catheter according to claim 9, wherein the fourth tubular body has a through-hole in a side wall on the second end side.

17. The atherectomy catheter according to claim 9, wherein the first tubular body has a balloon which expands outward from the side wall.

* * * * *